United States Patent
Hu et al.

(10) Patent No.: US 8,216,310 B2
(45) Date of Patent: Jul. 10, 2012

(54) POLYMER COMPOSITIONS SUITABLE FOR INTRAOCULAR LENSES AND RELATED METHODS

(75) Inventors: Can B. Hu, Irvine, CA (US); Michael D. Lowery, Vista, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 227 days.

(21) Appl. No.: 11/864,450

(22) Filed: Sep. 28, 2007

(65) Prior Publication Data
US 2009/0088839 A1    Apr. 2, 2009

(51) Int. Cl.
*A61F 2/16*    (2006.01)
(52) U.S. Cl. .................................................... 623/6.46
(58) Field of Classification Search ......... 623/5.11–6.62; 523/105–108
See application file for complete search history.

(56) References Cited

U.S. PATENT DOCUMENTS

| | | | |
|---|---|---|---|
| 5,217,491 A * | 6/1993 | Vanderbilt | 623/6.46 |
| 5,326,506 A * | 7/1994 | Vanderbilt | 264/1.7 |
| 6,432,137 B1 | 8/2002 | Nanushyan et al. | |
| 6,613,343 B2 * | 9/2003 | Dillingham et al. | 424/427 |
| 6,638,305 B2 * | 10/2003 | Laguette | 623/6.37 |
| 6,805,712 B2 * | 10/2004 | Lai et al. | 623/5.16 |
| 7,071,244 B2 * | 7/2006 | Liao | 523/106 |
| 2002/0071856 A1 | 6/2002 | Dillingham et al. | |
| 2004/0111151 A1 | 6/2004 | Paul et al. | |
| 2005/0038219 A1 | 2/2005 | Lai et al. | |
| 2005/0070626 A1 * | 3/2005 | Lowery | 523/113 |

FOREIGN PATENT DOCUMENTS

| | | |
|---|---|---|
| FR | 2779940 A1 | 12/1999 |
| WO | 2005055875 A2 | 6/2005 |
| WO | WO 2008/108524 | 9/2008 |

* cited by examiner

*Primary Examiner* — William H. Matthews
(74) *Attorney, Agent, or Firm* — Abbott Medical Optics Inc.

(57) ABSTRACT

A polymeric material with a molecular response time that makes it suitable for use near fragile body tissues. The polymeric material is useful for both low modulus and high modulus applications thereby simplifying the multi-part polymeric article manufacturing process and creating better integrated multi-part polymeric articles. Cross-linked polymers with different moduli may be obtained utilizing the same or similar starting materials but modifying the amount of catalyst, the amount of cross-linking agent, and/or the amount of methyl vinyl cyclics.

28 Claims, 1 Drawing Sheet

POLYMER COMPOSITIONS SUITABLE FOR INTRAOCULAR LENSES AND RELATED METHODS

FIELD OF THE INVENTION

Polymeric materials, devices, and methods in which the mechanical property of a polymer, such as the modulus, is selectable by altering the amount of catalyst used to prepare the polymer and/or by altering the amount of cross-linking agent or methyl vinyl cyclics is described herein.

BACKGROUND OF THE INVENTION

The human eye is a highly evolved and complex sensory organ. It is composed of a cornea, or clear outer tissue which refracts light rays en route to the pupil, an iris which controls the size of the pupil thus regulating the amount of light entering the eye, and a lens which focuses the incoming light through the vitreous fluid in the eye to the retina. The retina converts the incoming light to electrical energy that is transmitted through the brain to the occipital cortex resulting in a visual image. In a perfect eye, the light path from the cornea, through the lens and vitreous fluid to the retina is unobstructed. Any obstruction or loss of clarity within these structures, however, causes scattering or absorption of light rays resulting in diminished visual acuity. For example, the cornea can become damaged resulting in edema, scarring or abrasions, the lens is susceptible to oxidative damage, trauma and infection, and the vitreous fluid can become cloudy due to hemorrhage or inflammation.

As the body ages, the effects of oxidative damage caused by environmental exposure and endogenous free radical production accumulate resulting in a loss of lens flexibility and an accumulation of denatured proteins that slowly coagulate, reducing lens transparency. The natural flexibility of the lens is essential for focusing light onto the retina by a process referred to as accommodation. Accommodation allows the eye to automatically adjust the field of vision for objects at different distances. A common condition known as presbyopia results when the cumulative effects of oxidative damage diminish this flexibility reducing near vision acuity. Presbyopia usually begins to occur in adults during their mid-forties; mild forms are treated with glasses or contact lenses.

Lenticular cataracts are a lens disorder resulting from protein coagulation and calcification. There are four common types of cataracts: senile cataracts associated with aging and oxidative stress; traumatic cataracts which develop after a foreign body enters the lens capsule or following intense exposure to ionizing radiation or infrared rays; cataracts which are secondary to diseases such as diabetes mellitus or eye disorders such as detached retinas, glaucoma and retinitis pigmentosa; and cataracts resulting from medicinal or chemical toxicity. Regardless of the cause, the disease results in impaired vision and can lead to blindness.

Treatment of severe lens disease requires the lens' surgical removal or phacoemulsification followed by irrigation and aspiration. However, without a lens, the eye is unable to focus incoming light on the retina. Consequently, artificial lenses must be used to restore vision. Three types of prosthetic lenses are available: cataract glasses, external contact lenses and intraocular lenses (IOLs). Cataract glasses have thick lenses, are uncomfortably heavy and cause vision artifacts such as central image magnification and side vision distortion. Contact lenses resolve many of the problems associated with cataract glasses, but require frequent cleaning, are difficult to handle (especially for elderly patients with symptoms of arthritis), and are not suited for persons who have restricted tear production. Intraocular lenses are used in the majority of cases to overcome the aforementioned difficulties associated with cataract glasses and contact lenses.

There are four primary IOL categories: non-deformable, foldable, expansible hydrogels and injectable. Early non-deformable IOL implants were rigid structures composed of acrylates and methacrylates requiring a large incision in the capsular sac and were not accommodative. This large incision resulted in protracted recovery time and considerable discomfort for the patient. In an effort to reduce recovery time and patient discomfort, numerous small incision techniques and IOLs have been developed.

Subsequently, IOLs were designed for smaller incision implantation through the use of elastomeric compositions that could be rolled or folded, inserted into the capsular sac and then unfolded once inside. Occasionally, the fold of the IOL before insertion resulted in permanent deformation, which adversely affected the implants optical qualities. Further, while foldable IOLs eliminated the need for the large incision, foldable IOLs were not without drawbacks. In particular, both non-deformable and foldable IOLs are susceptible to mechanical dislocation resulting in damage to the corneal endothelium.

Another approach to small incision IOL implantation uses an elastomeric polymer that becomes pliable when heated to body temperature or slightly above. Specifically, the IOL is made pliable and is deformed along at least one axis, reducing its size for subsequent insertion through a small incision. The IOL is then cooled to retain the modified shape. The cooled IOL is inserted into the capsular sac and the natural body temperature warms the IOL at which point it returns to its original shape. The primary drawback to this type of thermoplastic IOL is the limited number of polymers that meet the exacting needs of this approach. Most polymers are composed of polymethylacyrlate which have solid-elastomeric transition temperatures above 100° C. Modifications of the polymer substrate require the use of plasticizers that may eventually leach into the eye causing harmful effects.

Dehydrated hydrogels have also been used with small incision techniques. Hydrogel IOLs are dehydrated before insertion and naturally rehydrated once inside the capsular sac. However, once fully rehydrated the polymer structure is notoriously weak due to the large amount of water absorbed. The typical dehydrated hydrogel's diameter will expand from 3 mm to 6 mm resulting in an IOL that is 85% water. At this water concentration the refractive index (RI) drops to about 1.36, which is unacceptable for an IOL since lower RI materials require the optic to be thicker to achieve a given optical power.

Modern acrylate IOLs generally possess excellent mechanical properties such as foldability, tear resistance and physical strength. Acrylate IOLs also are known to possess good optical properties (transparency, high refractive index, etc.) and biocompatibility. While pure acrylic IOLs have desirable mechanical, optical and biological properties, they may have unacceptable molecular response times such that the folded or compacted IOL may not unfold as quickly as desired. A pure acrylate IOL fabricated to have a relatively fast molecular response time may be extremely tacky and lack the desired mechanical strength. In this case, the resulting IOL may tear and/or the resulting self-tack can make unfolding difficult.

Pure silicone IOLs generally possess excellent mechanical, optical and biological properties similar to pure acrylate IOLs. Unlike acrylic IOLs, silicone IOLs generally possess faster molecular response times. In fact, the silicone IOLs may be so responsive that when folded small enough to be inserted through a 3 mm or smaller incision, the stored energy can cause the IOL to unfold more quickly than desired.

In light of the above considerations, it may be desirable to configure an intraocular lens so that the haptics have mechanical properties that differ from those of the optic to which they are attached. For example the optic may be fabricated from a material that has a relatively low modulus, while the haptics are made of another material having a relatively high modulus. However, not only can this two-material approach complicate supply requirements and the manufacturing process, there may also be incongruence between the two materials. The difference in materials may even result in a seam or even a weak physical link between the optic and haptic portions of the IOL. In addition, if the haptics protrude within an optic zone of the optic, the use of a different material having, for example, different refractive indices may lead to undesirable optical effects such as dysphotopsia or even undesirable optical aberrations.

Accordingly, there is a need for a polymeric material with a molecular response time that makes it suitable for use near fragile body tissues. There is also a need for ophthalmic devices in which one polymeric material is useful for both low modulus and high modulus applications to, inter alia, simplify the multi-part polymeric article manufacturing process and create better integrated multi-part polymeric articles in which the various parts have a common value of a property such as a refractive index.

SUMMARY OF THE INVENTION

The subject matter herein solves the problems associated with previous polymer materials by providing materials having moduli selectable by adjusting the amount of catalyst used to prepare the polymer. Alternatively or additionally, other mechanical properties of the material may be selected or adjusted. In some embodiments, the moduli selection may be affected by the hydride to vinyl ratio and/or the amount of cross-linking agent. Without wishing to be bound by theory, it is believed that methyl-vinyl cyclics ("MVCs"), which may be found in many catalysts, especially platinum catalysts, contribute to this phenomenon. In some embodiments, the impact on the modulus may be due to the presence of an inhibitor or stabilizer in the catalyst that reduces the hydride/vinyl ratio and/or prevent complete curing. In another embodiment, metals aside from platinum, more preferably transition metals, may be used. The siloxy materials discussed herein possess properties that make them suitable for the manufacture, for example, of both optic and haptic portions of IOLs. In such embodiments, the haptic and optic comprise a common polymeric material that may have a common value of a property, for example, having a common refractive index. The result is IOLs with a low modulus optic having a predetermined refractive index and, if prepared from the same components, well-integrated and resilient haptics. The IOLs will not damage the inserter cartridge or, more importantly, the surrounding ocular tissues. Low modulus polymers prepared as described herein also are ideal starting materials for many products implantable in patients (e.g., IOLs, augmentation implants). A common refractive index, within at least portions of both the optic and haptic portions, may advantageously reduce or eliminate glare, dysphotopsia, optical aberrations, and the like, by reducing or eliminating refractive index gradients at the boundary between the optic and haptic portions. In some embodiments, the optic of an ophthalmic device, such as of an IOL, has two or more portions that may be fabricated such that the portions have a common value of a property (e.g., a common material and/or a common refractive index), but have a different mechanical property, for example, a different moduli.

As an example, a siloxane component may be employed in the manufacturing of IOL materials. For example, the siloxane component may be a vinyl terminated siloxane. The vinyl terminated siloxane may comprise motifs including, but not limited to, divinyl terminated siloxanes, methacrylate functional siloxanes, acrylate functional siloxanes and combinations thereof. Preferably, the vinyl terminated siloxanes are selected from vinyl terminated diphenylsiloxane-dimethylsiloxane copolymers, vinyl terminated polyphenylmethylsiloxanes, vinylphenylmethyl terminated vinylphenylsiloxane-phenylmethylsiloxane copolymers, vinyl terminated polydimethylsiloxanes and combinations thereof.

One embodiment is an intraocular lens having an optic and a haptic with different moduli of elasticity and prepared from at least one common unsaturated silicone fluid, a hydride crosslinking agent and a platinum catalyst. In another embodiment, metals aside from platinum, more preferably transition metals may be used. In another embodiment, the optic and haptic also are prepared from at least one common hydride crosslinking agent and/or at least one common platinum catalyst. In some embodiments, the optic and haptic have a common optical and/or mechanical property, for example, a common refractive index.

Another embodiment is a method for forming an intraocular lens comprising an optic and a haptic and wherein said optic and said haptic have different moduli of elasticity but are prepared from at least one common unsaturated silicone fluid. The method may be practiced by combining at minimum: an unsaturated silicone fluid, a hydride crosslinking agent and a platinum catalyst to form the optic portion; combining the same unsaturated silicone fluid, a second hydride crosslinking agent and a second platinum catalyst to form the haptic portion; and, joining the optic and haptic portions to form an intraocular lens. A skilled artisan knows several ways to join or co-form optic and haptic portions such that a unitary IOL is formed.

Another embodiment is a method for increasing the modulus of elasticity of a polymer by combining an unsaturated silicone monomer, a hydride crosslinking agent and at least 0.1% by weight of a platinum catalyst and/or at least one MVC. In order to increase the modulus of elasticity, the amount of platinum catalyst and/or MVCs may be increased. A skilled artisan will appreciate the ability to encompass control the modulus of elasticity by varying the amount of platinum catalyst and/or MVCs used to prepare a polymer.

Any of the previously discussed embodiments may be practiced in conjunction with the following embodiments related to the silicone fluid, catalyst, MVC, and/or H/V ratio. In one embodiment, the common unsaturated silicone fluid may be a divinyl terminated silicone fluid, optionally having a pendant vinyl group. In another embodiment, the common unsaturated silicone fluid comprises monomers with the following Formula 1, wherein the sum of m and n is x; x is at least about 1, more preferably from about 5 to about 1200; y ranges from about 1 to about 500; z ranges from about 0 to about 500; the sum of x, y, and z is at least about 15; and R' and R" independently are optional pendant groups that may be selected from $CH_3$, $C_6H_5$, and $CH=CH_2$. In another embodiment, polymers can consist essentially of monomers depicted by Formula 1. In other embodiments, polymers can consist of greater than 50% w/w of monomers having the structure of Formula 1, or greater than 75% w/w of monomers having the structure of Formula 1, or greater than 85% w/w of monomers having the structure of Formula 1, or greater than 90% w/w of monomers having the structure of Formula 1, or greater than 95% w/w of monomers having the structure of Formula 1.

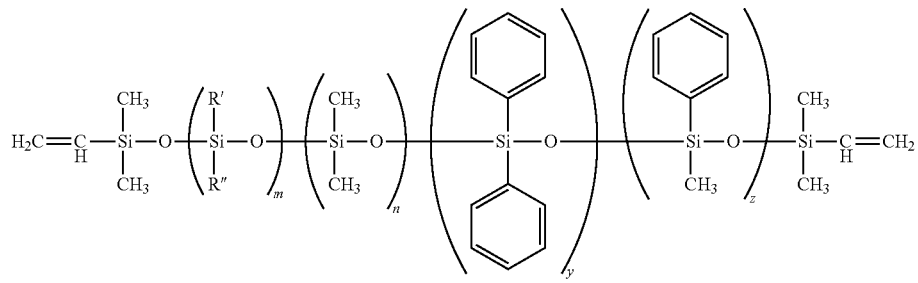

Formula 1

In another embodiment, the unsaturated silicone fluid may comprise tetravinyltetramethylcyclotetrasiloxane, 1,3-divinyltetramethyldisiloxane, or combinations thereof. In addition, the unsaturated silicone fluid also may include one or more of octamethylcyclotetrasiloxane, octaphenylcyclotetrasiloxane, or combinations thereof. In another embodiment, the hydride crosslinking agent may be phenyltris(dimethylsiloxy)silane; tetrakis(dimethylsiloxy)silane; 1,1,3,3-tetraisopropyldisiloxane; 1,1,3,3-tetramethyldisiloxane; 1,1,4,4-tetramethyldisilethane bis(dimethylsilyl)ethane; 1,1,3,3-tetramethyldisilazane; hydride terminated polyphenyl-(dimethylhydrosiloxy)siloxane; or combinations thereof. In another embodiment, the hydride crosslinking agent is phenyltris(dimethylsiloxy)silane.

In another embodiment, the platinum catalyst may be platinum carbonyl cyclovinylmethylsiloxane complex, platinumcyclovinylmethylsiloxane complex, platinum octanaldehyde complex, platinum octaoctanol compex, or combinations thereof. In another embodiment, the platinum catalyst may be present in an amount from about 0.1% to about 0.5% by weight.

In another embodiment, the MVC may be any methylvinyl siloxane, which includes cyclosiloxane and non-cyclosiloxane classes of materials. Nonlimiting examples of methylvinyl cyclosiloxane classes include tetramethylvinylcyclotetrasiloxane and pentamethylvinylcyclopentasiloxane. Non-cyclosiloxane classes include 1,3-tetramethyldisiloxane, divinyltetraphenyldisiloxane, 1,5-divinylhexamethyltrisiloxane, and 1,5-divinyl-3,3-diphenyltetramethyltrisiloxane. One example of an MVC is 1,3,5,7-tetravinyl-1,3,5,7-tetramethylcyclotetrasiloxane. In another embodiment, the MVC may be present in an amount of at least about 0.01% or at most about 1% by weight. It should be understood that for all polymer embodiments described in the present application, MVC may partially or completely substitute the catalyst, augment the catalyst or be used to alter the H/V ratio. MVC is believed to have an inversely proportional impact on the moduli of polymers prepared therewith.

In another embodiment, the unsaturated silicone monomer, said hydride crosslinking agent, said platinum catalyst, and/or said MVC form a cross-linked polymer having a H/V ratio of about 0.6 to about 1.1.

DEFINITION OF TERMS

The terms and phrases used herein shall have the following, non-limiting, definitions.

Elongation: As used herein, "elongation" refers to the act of lengthening or stretching a polymeric material.

Full Elongation: As used herein, "full elongation" refers to the act of lengthening or stretching a polymeric material or polymeric IOL to its elastic limit.

Intermediate Elongation: As used herein, "intermediate elongation" refers to the act of lengthening or stretching a polymeric material or polymeric IOL to a point between its original length and limit.

Glass Transition Temperature ($T_g$): As used herein, the "glass transition temperature ($T_g$)" refers to the temperature wherein a polymeric material becomes less elastic and more brittle. For soft polymeric materials described herein, $T_g$ typically is not measured since it may be as low as $-1000°$ C. or lower.

Mass percent As used herein, "mass percent" and "mass %" refer to the mass of monomer present in a polymer divided by the total weight of the polymer multiplied by 100. Mathematically, mass percent is represented by the following formula where $M_m$ is the mass of the monomer and $M_p$ is the mass of the corresponding polymer: $[M_m/M_p] \times 100 =$ Mass Percent.

Compression Modulus or Modulus of Elasticity: As used herein "modulus of elasticity" refers to the ratio of stress to strain As used herein, "compression modulus" refers to the ratio of compressive stress to compressive strain.

Moduli: As used herein, "moduli" refers to the plural form of modulus or modulus of elasticity.

Percent Elongation: As used herein, "percent elongation" refers to the length of an elongated polymer divided by the length of the original polymer. Mathematically, the percent elongation is represented by the following formula where L is the length of the elongated polymer and $L_0$ is the length of the corresponding non-elongated polymer: $[L/L_0] \times 100 =$ Percent Elongation.

Pliable: As used herein, "pliable" refers to the flexible nature of a polymeric material and to the flexibility of polymeric IOLs that can be folded, rolled or otherwise deformed sufficiently to be inserted through a 2 mm or less surgical incision.

kPa: As used herein, "kPa" refers to kilopascal, which is a unit of pressure or stress and is the equal to 1000×Newton per meter squared ($N/m^2$).

Resiliency: As used herein, "resiliency" refers to a polymeric material's or a polymeric IOL's inherent ability to return to its unstressed configuration following impact, deformation in an inserter, or the resulting deformation associated with the stress on impact, also referred to herein after as "rebound resiliency."

Refractive Index (RI): As used herein, "refractive index (RI)" refers to a measurement of the refraction of light of a material or object, such as an IOL. More specifically, it is a measurement of the ratio of the speed of light in a vacuum or reference medium to the speed of light in the medium under examination. The refractive index of a material or object typically varies with the wavelength of the light, a phenomenon sometimes referred to as dispersion.

Common Refractive Index: As used herein, "common refractive index" shall refer to the similarity of refractive indices between two materials. A common refractive index between two materials would be two materials with a difference in refractive index at a particular wavelength of less than or equal to 5%, or less than or equal to 2%, or less than or equal to 1%, or less than or equal to 0.2%.

Softness: As used herein, "softness" refers to a polymeric material's or a polymeric IOL's pliability as opposed to, for example, a polymethylmethacrylate (PMMA) IOL that is rigid and hard.

Ultimate Tensile Strength: As used herein, "ultimate tensile strength" refers to the maximum stress a material can withstand before fracture and is measured in psi (lb/in$^2$).

Clear Aperture: As used herein, "clear aperture" refers to the portion of an optic that limits the extent of the rays from an object that contributes to the conjugate image and is generally expressed as a diameter of a circle.

Common Polymeric Material: As used herein, "common polymeric material" refers to similarity of material composition between two objects or portions of an object. Two objects or portions of an object comprise a common polymeric material if the two objects or portions consist essentially of the same base polymer chain or have at least 50% w/w of the same base polymer chain, or 75% w/w of the same base polymer chain, or 85% w/w of the same base polymer chain, or 90% w/w of the same base polymer chain, or 95% w/w of the same base polymer chain, and, when present, the same cross-linking agent.

DETAILED DESCRIPTION OF THE INVENTION

Figure 1:
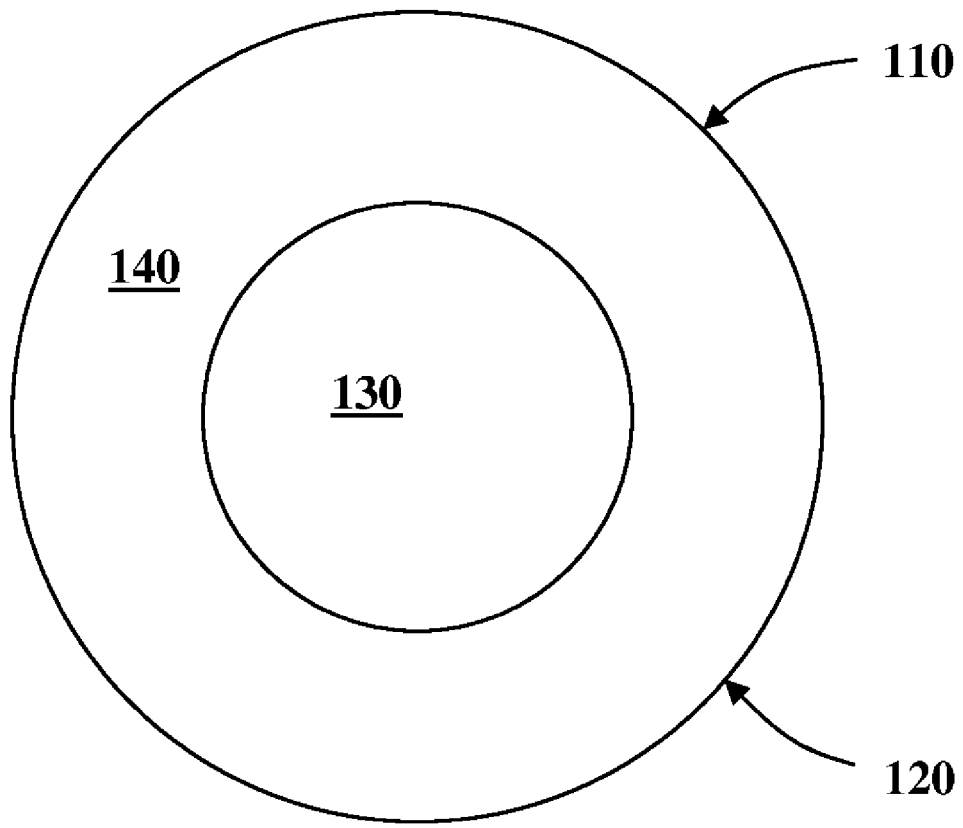
FIG. 1 is a front view of an intraocular lens having a clear aperture that comprises an inner portion and an outer portion disposed about said inner portion.

Polymer compositions with moduli or other mechanical properties that may be altered based, for example, on the amount of catalyst, cross-linking agent and/or MVC content are described herein. Also, low modulus materials produced as described herein exhibit mechanical qualities that make them excellent for implantation in living organisms, particularly animals, more particularly humans. Potential uses of the low modulus materials include, but are not limited to, IOL optics, breast or other augmentative implants, and controlled release devices (e.g., pharmaceutical formulations). The mechanical qualities and feel of the low modulus material make it possible to prepare bodily augmentation devices that are implantable in a living organism, for example, breast implants containing little or no liquid.

As for IOLs, it is desirable they can be folded, rolled or otherwise deformed such that they can be inserted through small incisions. Furthermore, in order to reduce patient trauma and post surgical recovery time, the IOL preferably comprises a responsive polymer that unfolds in a controlled manner. To meet these requirements, the polymers preferably have minimal self tack and do not retain excessive amounts of stored mechanical energy. However, if the IOL is too thin, or the polymer lacks sufficient mechanical strength, it may be too fragile and easily dislocated or damaged during or after the insertion process.

Historically, foldable IOL materials have been designed to be tough (tensile strength of greater than 750 pounds per square inch [psi]) and with a relatively high percent elongation (greater than 100%). These properties give the IOL sufficient toughness such that the IOL does not tear from the forces experienced during insertion through a 2.6 to 3.2 mm incision Presently available foldable IOLs include, among others, Sensar® (Advanced Medical Optics, Santa Ana Calif.), an acrylic IOL having a tensile strength of about 850 psi and an elongation at break of about 140%; SLM-2® (Advanced Medical Optics, Santa Ana Calif.), a silicone IOL having a tensile strength of about 800 psi and an elongation at break of about 230%; and AcrySof® (Alcon Laboratories, Fort Worth, Tex.) having a tensile strength of about 1050 psi. All three IOLs are suitable for insertion through incision sizes of about 2.6 mm or greater. The polymers described herein are soft to very soft and may be foldable.

Flexibility in monomer selection, which provides for control over the material's mechanical, optical and/or thermal properties are provided herein. For example, the ability to adjust a material's refractive index (RI) and mechanical properties is important in designing ultra-small incision IOLs. Also, hydrophobic siloxy materials have demonstrated excellent ocular biocompatibility. Thus, it surprisingly has been discovered that by utilizing the silicone materials in the preparation of IOL materials, an IOL optic can be made that has properties permitting its passage through an ultra small incision without damage to the IOL, the inserter cartridge, or the eye. In addition, the IOL may have at least one resilient haptic that shares a common siloxy monomer with the optic.

Silicones have unique properties derived from the inherent flexibility of the siloxane bond. The alternating silicon-oxygen polymer backbone of siloxanes makes them remarkably more flexible than their organic counterparts that have a carbon-oxygen backbone. This property of siloxanes results in low glass-transition temperatures ($T_g$) and excellent flexibility. Furthermore, a low initial modulus is another important attribute of the novel siloxanes. In order to pass through the insertion cartridge, a conventional refractive IOL must be capable of elongating up to about 100%. Therefore, it is important that the initial modulus be at optimum levels. A low initial modulus translates to low stimulus required to express the IOL through the cartridge. Further, when the appropriate amounts of selected siloxanes, cross linkers and catalysts are combined, the resulting material has the flexibility and modulus required to make, for example, the optic portion of an IOL suitable for insertion through a small incision without harming the IOL, the inserter cartridge or the eye.

In some embodiments, an intraocular lens comprises an optic and a haptic made from a common polymeric material so that they also have a common refractive index; however, the optic and haptic have mechanical property that is different for each. In some embodiments, the IOL may be formed according to an embodiment so that the optic and haptic have different moduli of elasticity. For example, an accommodating IOL may be formed so that the optic has a lower modulus than the haptic, thus allowing the relatively stiff haptic to protrude inside the relatively soft optic without causing unwanted reflections due to a refractive index mismatch at interfaces between the optic and the protruding haptic. Examples of accommodating IOLs having a stiffer protruding haptic are disclosed in co-pending U.S. patent application Nos. 11/618,411 and 11/618,325, which are herein incorporated by reference in their entirety. The difference in moduli between the haptic and optic may be provided by an adjustment in the amount of cross-linker and/or catalyst and/or MVC content of each IOL component. Embodiments herein may be used to provide IOL's in which at least the optic thereof has a modulus that is less than about 100 kPa, less than 75 kPa, or even less than 50 kPa or 25 kPa. The stiffness of the haptic may be greater than 500 kPa, or greater than 3000 kPa, depending on the particular design requirements. In some embodiments, the modulus of the haptic is greater than that of the optic by at least 50%, by at least 150%, by at least 250%, or by at least 500%. In some embodiments, the modulus may vary continuously over at least some interface regions between the haptic and the optic, for example, to provide a particular performance or stress distribution over the IOL in reaction to an external force on the IOL (e.g., an ocular force produced by the capsular bag, zonules, or ciliary muscle of an eye into which the IOL is inserted).

In some embodiments, an ophthalmic lens, such as an intraocular lens, comprises an optic having a clear aperture that comprises an inner portion and an outer portion disposed about said inner portion. For example, referring to FIG. 1, an intraocular lens 100 comprises an optic 110 having a clear aperture 120 that comprises an inner portion 130 and an outer portion 140 disposed about inner portion 130. The inner portion and outer portion comprise a common polymeric material and may have a common refraction index; however, the inner portion has a modulus that is different from that of the outer portion. The difference in modulus may be selected, for example, to control the amount and/or form of deformation of the optic in reaction to an external force such as an ocular force produced by the capsular bag, the zonules, and/or the ciliary muscle of an eye into which the optic is placed. In some embodiments, the refractive index may also vary between the zones, for example, to control aberrations of the optic in a stressed or unstressed state.

The modulus of the inner portion of the optic may be greater than or less than that of the outer portion, depending of the particular design requirements. In some embodiments, the optic comprises three or more zones disposed within the clear aperture of the optic. In other embodiments, the modulus of at least portions of the optic may vary continually, for example, by producing a catalyst gradient throughout a polymeric fluid used to form the optic. In some embodiments, the zones of the optic may have an ellipsoid or similar shape, such that the modulus varies from the center of the optic outward in a three-dimensional manner. Alternatively or additionally, the variation in modulus of the zones may vary in a two dimensional manner, for example, forming concentric rings as the modulus varies in radial direction from the optical axis of the optic. The difference in modulus between two zones of the optic may be greater than or equal to 5%, or greater than or equal to 15%, or greater than or equal to 25%, or greater than or equal to 50%, depending on the number of zones and the desired performance of the optic under a given loading force.

The materials described herein may have low initial moduli and a low glass transition temperature ($T_g$). Moreover, the IOLs may be multifocal (i.e. refractive or diffractive), accommodating (i.e. deformable or movable under the normal muscle movements of the human eye), highly biocompatible and have RIs ranging from about 1.40 to about 1.56, preferably from about 1.41 to about 1.49, for light in the visible wavelengths. These and other objects described herein may be achieved by providing an unsaturated terminated silicone fluid and cross-linking it using a hydride cross-linking agent and platinum catalyst. In another embodiment, transition metals aside from platinum, more preferably transition such as, but not limited to, rhodium and palladium, may be used. Silicone fluids that may be cross-linked to prepare polymers with different moduli simply by varying the amount of cross-linking agent and/or catalyst and/or MVC content are disclosed.

The unsaturated terminated siloxanes are preferably vinyl terminated siloxanes, more preferably multi-vinyl terminated. Non-limiting examples include vinyl terminated diphenylsiloxane-dimethylsiloxane copolymers, vinyl terminated polyphenylmethylsiloxanes, vinyl terminated phenylmethylsiloxane-diphenyldimethylsiloxane copolymers, vinyl terminated polydimethylsiloxanes and methacrylate, and acrylate functional siloxanes. Other suitable silicone materials are disclosed in U.S. Pat. No. 6,361,561, the entirety of which is incorporated herein by reference. Representative materials can be obtained from Gelest, Inc. (Morrisville, Pa.) or synthesized using methods known to those skilled in the art.

In one embodiment, the unsaturated terminated siloxane is a vinyl terminated siloxane comprising monomers comprising the structure depicted in Formula 1 below. The polymers described herein can consist essentially of monomers comprising the structure of Formula 1. In other embodiments, polymers can consist of greater than 50% w/w of monomers having the structure of Formula 1, or greater than 75% w/w of monomers having the structure of Formula 1, or greater than 85% w/w of monomers having the structure of Formula 1, or greater than 90% w/w of monomers having the structure of Formula 1, or greater than 95% w/w of monomers having the structure of Formula 1. The values for x, y, and z in Formula 1 will vary depending on, for example, the desired RI of the lens; and, in Formula 1, x is equal to the sum of m and n and is preferably at least about 1. Preferably, IOLs described herein have an RI of at least 1.40, more preferably at least 1.43. For example, if an IOL having a refractive index ("RI") of 1.43 is desired, the x:y:z ratio may be approximately 30:1:1; a x:y:z ratio of about 12:1:2 will result in an IOL having a RI of approximately 1.46. Skilled artisans can prepare an IOL having a desired RI, optical clarity and mechanical properties by adjusting the x:y:z ratio using skills known in the art and without undue experimentation. In one embodiment, x ranges from about 10 to about 1200, y ranges from about 1 to about 500, z ranges from 0 to about 500, and the sum of x, y, and z is from about 100 to about 1500. In another embodiment, x+y+z has a minimum value of about 200 in order to provide a high softness polymer (e.g., when required for optic portions of an IOL). R' and R" are optional pendant groups independently selected from $CH_3$, $C_6H_5$, and $CH=CH_2$.

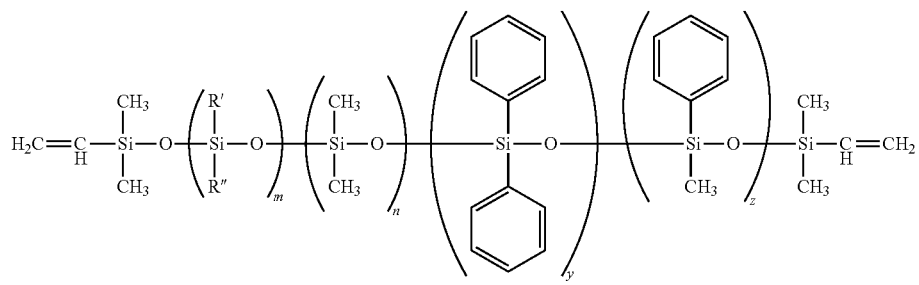

Formula 1

When z is equal to zero, the values for x and y still will vary depending on, for example, the desired RI of the lens and the unsaturated terminated siloxane will comprise monomers with the structure depicted in Formula 2 below (also referred to as "AMO silicone fluid). In one embodiment, polymers can consist essentially of monomers with the structure of Formula 2. In other embodiments, polymers can consist of greater than 50% w/w of monomers having the structure of Formula 2, or greater than 75% w/w of monomers having the structure of Formula 2, or greater than 85% w/w of monomers having the structure of Formula 2, or greater than 90% w/w of monomers having the structure of Formula 2, or greater than 95% w/w of monomers having the structure of Formula 2. For an IOL with a RI of 1.43, the x:y ratio may be approximately 18:1; a x:y ratio of 5:1 will result in an IOL having a RI of approximately 1.46. Skilled artisans can prepare an IOL having a desired RI, optical clarity and mechanical properties by adjusting the x:y ratio using skills known in the art and without undue experimentation. In one embodiment, x is at least 1, more preferably from about 5 to about 10, y ranges from about 3 to about 8, and the sum of x and y is about 15. In another embodiment, x+y will have a minimum value of 400 for applications that require high softness. R' and R" are optional pendant groups independently selected from $CH_3$, $C_6H_5$, and $CH=CH_2$.

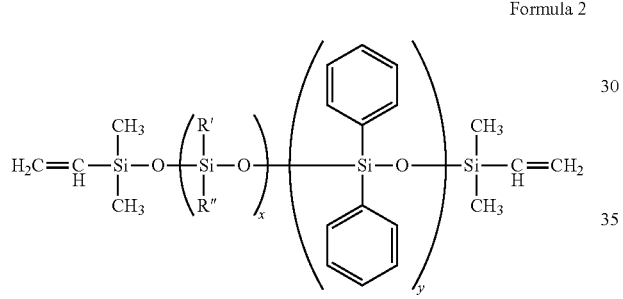

Formula 2

Optionally, a number of ultraviolet (UV) and blue light absorbing dyes can be added to the silicone polymers described herein. For example, the silicone IOLs may include 0.1 to 1.5 mass % of UV and blue light absorbing compounds such as benzophenone and benzotriazole-based UV light absorbers or blue light blocking dyes including azo and methine yellow, which selectively absorb UV/blue light radiation up to about 450λ. See, for example, U.S. Pat. Nos. 5,374,663; 5,528,322; 5,543,504; 5,662,707; 6,277,940; 6,310,215 and 6,326,448, the entire contents of which are incorporated herein by reference.

A variety of initiators for polymerization reactions are employed herein. In one non-limiting embodiment, peroxide initiators are used. Examples of peroxide initiators include, without limitation, about 0.100 to about 1.50 mass % of di-tert-butyl peroxide (Trigonox® a registered trademark of Akzo Chemie Nederland B.V. Corporation Amersfoort, Netherlands) or 2,5-dimethyl-2,5-bis (2-ethylhexanoylperoxy) hexane. It should be noted that peroxide initiators initiate the cross-linking of vinyl groups on monomers (e.g., those on divinyl-terminated silicone monomers). While this can help facilitate the cross-linking of the silicone monomers, at least some of the hydride groups must still be cross-linked as described herein.

One or more monomers may be cross-linked utilizing one or more hydride-containing cross-linkers such as, but not limited to: nonpolymetric X-linkers such as phenyltris(dimethylsiloxy)silane (Formula 3 below), tetrakis(dimethylsiloxy)silane (Formula 4 below), 1,1,3,3-tetraisopropyldisiloxane, 1,1,3,3-tetramethyldisiloxane, 1,1,4,4-tetramethyldisilethane bis(dimethylsilyl)ethane, 1,1,3,3-tetramethyldisilazane; hydride terminated polymeric X-linkers with different molecular weights such as DMS-H03, DHS-H11 to DMS-H41, hydride terminated polyphenyl-(di-methylhydrosiloxy)siloxane (HDP-111, Formula 5 below, wherein W is about 5 to about 50); HPM-502, which are commercially available from Gelest; nonhydride terminated polymeric cross-linkers such as XL-103, XL-110 XL-111, XL-112, XL-115, which are commercially available from Nusil; and HMS-013, HMS-031, HMS-082, HMS-301, HMS-991, which are commercially available from Gelest. Other cross-linkers such as hydride Q resins may also be used to improve the mechanical properties of the gels. The softness of the final gel formulations depends on the relative amount of cross-linker to vinyl silicone fluid (i.e. H/V [hydride-vinyl] ratio).

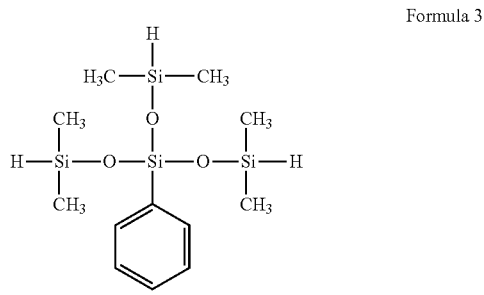

Formula 3

Phenyltris(dimethylsiloxy)silane

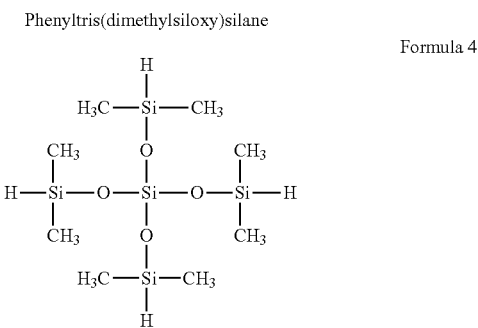

Formula 4

Tetrakis(dimethylsiloxy)silane

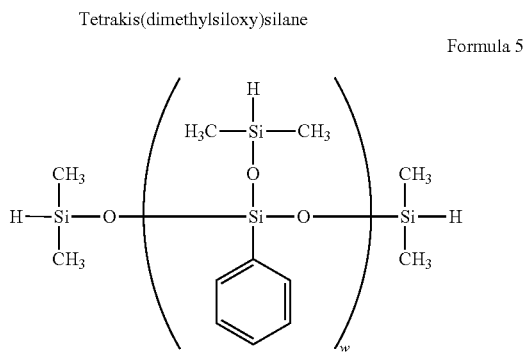

Formula 5

Hydride-terminated Polyphenyl-(di-methylhydrosiloxy)siloxane

Properties of the silicone materials such as modulus, percent weight loss may be changed by varying the ratio of hydride and vinyl contents (H/V ratio) in the silicone fluids. Vinyl content of a silicone fluid may be determined by, for example, the GPC method, titration, or NMR (nuclear magnetic resonance spectroscopy). By varying the ratio of hydride primarily from the cross-linker and vinyl primarily from the vinyl silicone fluid, silicone materials with different moduli may be obtained. In certain embodiments, it is preferable for the H/V ratio to be at least about 0.1, more preferably at least about 0.5, more preferably about 0.6, more preferably about 0.7, more preferably about 0.8, more preferably about 0.9, more preferably about 1.0, more preferably about 1.1, more preferably about 1.25, and more preferably at most about 1.5.

It was also surprisingly discovered herein that the modulus of material is affected by the amount of catalyst and/or methyl-vinyl cyclics ("MVCs") as well. Specifically, as the amount of catalyst and/or MVCs is increased, the modulus of the material also increases until a peak modulus is reached. After the peak modulus is reached, the modulus begins to level off or, in many cases, decrease. A relationship between post-extraction modulus and % catalyst used for three H/V ratios: 0.7, 1.125 and 1.55 was determined and showed that the point at which the modulus begins to level off or decrease depends not only on the amount of catalyst or MVCs, but also on the monomers and cross-linking agents (which may impact H/V ratio) used to prepare the polymer.

In general, platinum-containing catalysts work well. Exemplary platinum catalyst include platinum-tetravinyltetramethylcyclotetrasiloxane complex, platinum carbonyl cyclovinylmethylsiloxane complex, platinum cyclovinylmethylsiloxane complex, platinum octanaldehyde/octanol complex. Many different platinum catalysts may be used depending on, inter alia, the desired pot life. Preferably, the platinum catalyst is used in amounts by weight of at least about 0.01%, more preferably at least about 0.05%, even more preferably at least about 0.1%. Preferably, the platinum catalyst is used in amounts of about 1% or less, more preferably about 0.75% or less, even more preferably about 0.5% or less, even more preferably about 0.4%, even more preferably about 0.3%, even more preferably about 0.2%.

In addition to platinum catalysis, other metal catalysis can be used. In some embodiments, transition metals can be used as catalysts, more specifically, palladium and rhodium catalysts can be used. Complexes and salts of metal catalysts can be used. An example of a transition metal complex used as a catalyst is tris(dibutylsulfide) rhodium trichloride.

Without wishing to be bound by theory, one reason for the impact of some catalysts, especially platinum catalysts, on the modulus may be due to the presence of an inhibitor or stabilizer that may reduce the hydride/vinyl ratio and/or prevent complete curing. An example of such an agent is a MVC such as cyclovinylmethylsiloxane (e.g., 1,3,5,7-tetravinyl-1, 3,5,7-tetramethylcyclotetrasiloxane). It is worthwhile to note that the effects of catalyst amounts on modulus were independent of curing time. While MVCs sometimes are used as stabilizers in catalysts to, for example, prevent keep platinum suspended in solution, the MVCs typically are present in such small amounts that they are inert.

This aspect unexpectedly was discovered when the platinum catalyst level for a polymer was increased to levels significantly higher than conventionally used (e.g., up to 50 ppm versus a more traditional 10 ppm or less). A skilled artisan would expect that as catalyst concentration increases, curing time decreases and polymer cross linking increases. The skilled artisan also would expect this to lead to a more rigid or firm polymer (even assuming curing temperature is the same). When the catalyst was increased to atypical levels, a significant decrease in curing time was observed.

Contrarily, however, the resulting polymer was far less rigid and less firm than expected. Without wishing to be bound by theory, it is believed that when excessive amounts of catalyst were used, the corresponding increase in MVCs allowed them to become reactive ingredients and end-cap the hydrides on the cross-linkers, which resulted in more free ends on the structural polymers. The additional free ends provide a less-cross-linked and, therefore, less rigid polymer. As a skilled artisan would appreciate, such a polymer is ideal for preparing many products including, but not limited to, products implantable in patients (e.g., IOLs, augmentation implants).

Herein, the MVC may be present in an amount of at least about 0.01%, about 0.05%, about 0.1%, about 0.11%, about 0.15%, about 0.2%, or about 0.25% by weight; to at most about 1%, about 0.75%, about 0.5%, about 0.4%, about 0.39%, about 0.35%, or about 0.35% by weight. It should be understood that for all polymer embodiments described herein, the MVC may partially substitute the catalyst in any proportion or amount including completely or the MVC may augment the catalyst. The MVC is believed to have an inversely proportional impact on the moduli of polymers prepared therewith. It will be appreciated that all embodiments described herein, including IOLs and methods for producing them, may incorporate the teachings regarding MVCs and their relationship to the moduli of polymer articles prepared therefrom.

When used for IOL optic portions, a polymer with a low initial modulus, as described herein, facilitates a more easily inserted IOL by reducing the force required to express the polymer IOL through an inserter cartridge. In addition, since the same starting materials may be used for both optic and haptic portions (only varying the H/V ratio and/or % catalyst or MVC), the material supply and manufacture of IOLs is simplified. An added benefit of using the same starting materials is that the resulting optic and haptic portions will be more compatible thereby facilitating more robust and/or seamless fusion.

Example 1

Preparation of Polymer Discs

In one method for making a polymer, 129.43 grams of octaphenylcyclotetrasiloxane was placed in a preheated 1000 mL reaction kettle at 105° C. (+/−10° C.). The mechanical stirrer was turned on and the whole system purged with nitrogen for at least 30 minutes. Next, 666.16 grams of octamethylcyclotetrasiloxane and 4.50 grams of 1.3 divinyl tetramethyl disiloxane were added to the reaction kettle. Then, 3.14 grams of tetramethylammoniun siloxanolate was added to the reaction kettle. Stirring continued for at least 18 hours at 105° C. (+/−10° C.). The temperature of the kettle was then raised to 150° C. (+/−20 C) for at least 5 hours. After cooling, a clear silicone fluid was filtered through a 0.2 micron filter.

A Pope 2" Wiped-Film stills unit was used to remove the volatile components of the above silicone fluid by setting the chiller temperature to 5° C., still body temperature to 160° C., the vacuum range to 0.8-2.2 torr and the rotor speed to 70 RPM. A total of 11.68% of the volatile components were removed at three different locations. GPC scans before and after wiped-film process showed the effectiveness of this step to remove volatile components. The efficacy of the wiped-film process was clearly demonstrated by the GPC scans as shown in FIG. 2. Most of the low molecular weight species were removed by this process. Depending on the application, this process may be important for performance since it significantly reduces the amount of leachable species in the resulting polymer product.

Next, 0.125 grams of 2-(3'-t-butyl-2'-hydroxy-5'-vinyl-phenyl)-5-chlorobenzotriazole (UVAM) was added to 50 grams of the above silicone fluid. After centrifugal mixing, the fluid was placed in the 60° C. oven for 2 to 3 days until the UVAM was completely dissolved in the silicone fluid to make a "0.25% UVAM silicone fluid". Varying amounts of a catalyst, in this case platinum-tetravinyltetramethylcyclotetrasiloxane complex, were added to 20 grams of the 0.25% UVAM silicone fluid and centrifugally mixed to form "Part A" of the silicone fluid. The final catalyst concentration of three otherwise identical silicone fluids was, by weight, 0.1%, 0.3% and 0.5%. "Part B" of the silicone fluid was prepared by mixing 0.0681 grams of phenyltris(dimethylsiloxy)silane with 5 grams of the 0.25% UVAM silicone fluid.

Next, 5 grams each of Part A and Part B were poured into a Teflon mold and cured in a 140° C. oven for 10 minutes to prepare "discs". After soxhlet extraction, some of the discs were placed in a fume hood overnight and then placed in a 60° C. oven for 2 days before modulus testing. The modulus of these pre- and post-extraction discs was measured using a Q800 DMA (TA Instruments). After loading a sample on the holder, the temperature was raised to 35° C. and allowed to equilibrate for 5 minutes before testing. Ramp force was applied to the disc at 1 Newton/min to a maximum of 9 Newton. Modulus may be determined by calculating the slope of two points from the resulting curve.

To demonstrate the impact of catalyst concentration on the modulus of a polymer at a fixed H/V ratio of 0.7, the three polymers with 0.1%, 0.3% and 0.5% by weight catalyst were tested. For each catalyst concentration, some discs underwent static IPA extraction (soxhlet) for one day and were dried in a vacuum oven for two days before modulus measurement. Curing conditions were also varied. The results, which are summarized in Table 1, show that a polymer's modulus is sensitive to the amount of catalyst used to prepare the polymer. In this case, as the amount of catalyst was increased, the modulus of the material was reduced. Discs with 0.5% catalyst were very soft and had a tendency to delaminate, therefore, no accurate modulus measurement could be obtained.

TABLE 1

Modulus of silicone samples at different catalyst levels and curing history

| Curing Conditions | 0.1% catalyst Modulus, KPa | | 0.3% catalyst Modulus, KPa | | 0.5% catalyst Modulus, KPa |
|---|---|---|---|---|---|
| | Before extraction | After static extraction | Before extraction | After static extraction | |
| 140° C., 10 mins | 155 | 157 | 54 | 53 | Too soft to test |
| 140° C., 10 mins 60° C., 1 day | 151 | 135 | 51 | 54 | |
| 140° C., 10 mins 60° C., 3 days | 151 | 162 | 53 | 59 | |
| 140° C., 10 mins 60° C., 5 days | 150 | 154 | 50 | 57 | |

Example 2

A gel was prepared in accordance with Example 1; however, instead of using platinum tetravinyltetramethylcyclotetrasiloxane complex, 0.3% platinum carbonyl cyclovinylmethylsiloxane complex was used to prepare the silicone gel. The pot life of the silicone gel increased 1 hour (from 7 hours to 8 hours) without significantly changing the modulus of the final gel.

Example 3

A divinyl terminated silicone fluid in accordance with Example 1; however, it was prepared using two different cross-linkers, phenyltris(dimethylsiloxy)silane (SIP) and tetrakis-(dimethylsiloxy)silane (SIT). The amount of cross-linker used was varied to prepare fluids with four different H/V ratios. Vinyl content of the silicone fluids was determined by the GPC method. A platinum-cyclovinylmethylsiloxane complex was used to cure the polymers. Moduli of the sixteen polymers was measured both pre-extraction and post static extraction. It was found that by varying the amount of cross-linker used in the vinyl fluid, silicone materials with different moduli could be obtained. It was also surprising to find that the modulus of the materials was also affected by the amount of catalyst. The curing time did not appear to be a factor in the modulus of the cured samples. The specifics of the experiment follow.

Divinyl silicone fluid (B36C) was mixed with two cross-linkers, SIP and SIT at four different (H/V) ratios and with 0.3% catalyst. In all samples, enough UVAM (2-(3'-t-butyl-2'-hydroxy-5'-vinyl-phenyl)-5-chlorobenzotriazole) was added to the silicone fluids to provide a final concentration of 0.25%. Silicone discs were cured at 140° C. for 10 minutes Some of the discs also went through static IPA extraction for one day and were dried in a vacuum oven for two days before modulus measurement. Moduli of these silicone samples before and after IPA extraction were determined using a Q800 DMA from TA instruments. Results of the compression modulus (average of 2 discs in each condition) and percentage weight loss are summarized in the following two tables, Tables 2 and 3.

TABLE 2

Compression modulus of silicone samples at different H/V ratios

| | Modulus with SIP Cross-Linker (KPa) | | Modulus with SIT Cross-Linker (KPa) | |
|---|---|---|---|---|
| H/V ratio | Before Extraction | After Static Extraction | Before Extraction | After Static Extraction |
| 1.5 | 104 | 196 | 496 | 631 |
| 1.0 | 588 | 669 | 544 | 635 |
| 0.7 | 64 | 73 | 82 | 121 |
| 0.5 | Too soft to test | | Too soft to test | |

TABLE 3

Percentage weight loss of silicone samples after 1 day static IPA extraction

| H/V ratio | SIP Cross-Linker (%) | SIT Cross-Linker (%) |
|---|---|---|
| 1.5 | 3.6 | 1.9 |
| 1.0 | 2.3 | 2.1 |
| 0.7 | 5.3 | 5.6 |

The vinyl terminated silicone fluids may have degrees of polymerization of, for example, 200, 400, 600, 800, 1000 and 1200. The polymer of Example 1 has a degree of polymerization of about 400 and a refractive index of about 1.43. An exemplary polymer with a degree of polymerization of about 600 comprises, by weight, about 86.69% octamethylcyclotetrasiloxane, about 12.92% octaphenylcyclotetrasiloxane, about 0.38% 1,3-divinyltetramethyldisiloxane, and 0.25% tetramethylammoniun siloxanolate. In addition, 0.25% 2-(3'-t-butyl-2'-hydroxy-5'-vinyl-phenyl)-5-chlorobenzotriazole subsequently may be added using the procedures of Example 1. An exemplary polymer with a degree of polymerization of about 800 comprises, by weight, about 86.78% octamethylcyclotetrasiloxane, about 12.93% octaphenylcyclotetrasiloxane, about 0.29% 1,3-divinyltetramethyldisiloxane, and 0.25% tetramethylammoniun siloxanolate. In addition, 0.25% 2-(3'-t-butyl-2'-hydroxy-5'-vinyl-phenyl)-5-chlorobenzotriazole subsequently may be added using the procedures of Example 1.

Example 4

In order to test the impact of MVCs on a polymer, a first polymer composition was prepared with 0.1% catalyst while a second polymer composition was prepared with 0.1% catalyst and 0.4% MVC (equivalent to about 0.5% catalyst). Aside from catalyst/MVC content, the polymer compositions were otherwise identical. Also, six samples of each polymer composition were cured at three different curing conditions (i.e., 2 samples of each polymer at each curing condition). Two samples of the first polymer and two samples of the second polymer were cured at 140° C. for 10 minutes. Two samples of each polymer composition also were cured at 140° C. for 3 hours. And, two samples of each polymer composition also were cured at 140° C. for 10 minutes followed by curing at 60° C. for 5 days. The average modulus for the first polymer composition was in the range of about 132 to about 195 KPa, which is similar to the 0.1% catalyst-containing polymer results shown in Table 1. None of the samples of the second polymer composition prepared with 0.1% catalyst and 0.4% MVC could be removed from the curing trays for modulus measurement since they were too soft to test. As can be appreciated, increasing the amount of catalyst/MVC may increase the reactivity of different species and may thereby reduce the amount of unreacted species. An exemplary MVC, e.g. 1,3,5,7-tetravinyl-1,3,5,7-tetramethylcyclotetrasiloxane, may be purchased from Gelest (SIT 7900.0) or United Chemical Technologies (UCT Catalog No. T2160).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope described herein are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate and do not pose a limitation on the scope otherwise claimed. No language in the specification should be construed as indicating that any non-claimed element is essential to the embodiments disclosed herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode, if known to the inventors at the time of filing. Of course, variations on these described embodiments will become apparent to those of ordinary skill in the art upon reading the foregoing description. The inventor expects skilled artisans to employ such variations as appropriate. Practice of modifications and equivalents of the subject matter recited in the claims is expected. Moreover, any combination of the above-described elements in all possible variations thereof is encompassed herein unless otherwise indicated or otherwise clearly contradicted by context.

Furthermore, references have been made to patents and printed publications throughout this specification. Each of the above-cited references and printed publications individually are incorporated herein by reference in their entirety.

In closing, it is to be understood that the embodiments disclosed herein are for illustrative purposes. Other modifications may be employed and are within the scope of the claims. Thus, by way of example, but not of limitation, alternative configurations may be utilized in accordance with the teachings herein. Accordingly, the teachings herein are not limited to that precisely as shown and described.

We claim:

1. An intraocular lens comprising an optic and a haptic,
   wherein an interface portion of the haptic protrudes inside an interface portion of the optic,
   wherein said interface portion of said optic has a lower modulus of elasticity than said interface portion of said haptic,
   wherein the entire optic has a modulus of elasticity of less than about 100 kPa,
   wherein said interface portion of said optic and said interface portion of said haptic comprise a common polymeric material and have a common refractive index, and
   wherein the entirety of the optic is capable of forming a focused image when the intraocular lens is implanted in a capsular bag of an eye.

2. An intraocular lens according to claim 1, wherein said optic and said haptic are formed from a hydride cross-linking agent that is the same for said optic and said haptic.

3. An intraocular lens according to claim 1, wherein said optic and said haptic are formed from a catalyst that is the same for said optic and said haptic.

4. An intraocular lens according to claim 1, wherein said common polymeric material is formed from a divinyl terminated silicone fluid.

5. An intraocular lens according to claim 4 wherein said common polymeric material is formed from a polymer having a pendant vinyl group.

6. An intraocular lens according to claim 1, wherein said common polymeric material is formed from polymers having Formula 1:

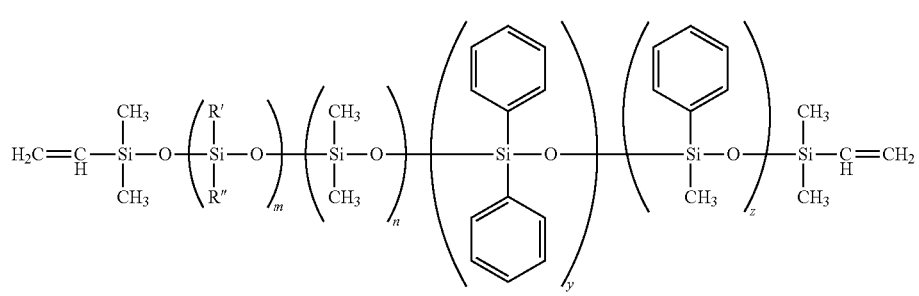

Formula 1 wherein the sum of m and n is x, x ranges from about 1 to about 1200, y ranges from about 1 to about 500, and z ranges from about 0 to about 500, the sum of x, y, and z is at least about 15, and R' and R" independently are optional pendant groups that may be selected from the group consisting of $CH_3$, $C_6H_5$, and $CH=CH_2$.

7. An intraocular lens according to claim 1, wherein said common polymeric material is formed from monomers selected from the group consisting of octamethylcyclotetrasiloxane, octaphenylcyclotetrasiloxane, tetravinyltetramethylcyclotetrasiloxane, 1,3-divinyltetramethyldisiloxane, and combinations thereof.

8. An intraocular lens according to claim 2, wherein said hydride crosslinking agent is selected from the group consisting of phenyltris(dimethylsiloxy)silane; tetrakis(dimethylsiloxy)silane; 1,1,3,3-tetraisopropyldisiloxane; 1,1,3,3-tetramethyldisiloxane; 1,1,4,4-tetramethyldisilethane bis (dimethylsilyl)ethane; 1,1,3,3-tetramethyldisilazane; hydride terminated polyphenyl-(di-methylhydrosiloxy)siloxane; and combinations thereof.

9. An intraocular lens according to claim 3, wherein said catalyst is selected from the group consisting of a transition metal catalyst, platinum carbonyl cyclovinylmethylsiloxane complex, platinumcyclovinylmethylsiloxane complex, platinum octanaldehyde complex, platinum octaoctanol compex, and combinations thereof.

10. An intraocular lens according to claim 3, wherein said catalyst is a platinum catalyst that is present in an amount from about 0.1% to about 0.5% by weight.

11. An intraocular lens according to claim 2, further comprising a platinum catalyst; further wherein said common polymeric material, said hydride crosslinking agent and said platinum catalyst form a cross-linked polymer having a H/V ratio of about 0.6 to about 1.1.

12. An intraocular lens according to claim 1, wherein the intraocular lens is movable under the normal muscle movement of the human eye.

13. An intraocular lens according to claim 1, wherein the intraocular lens is deformable under the normal muscle movement of the human eye.

14. An intraocular lens according to claim 1, wherein the interface portion of the optic and the interface portion of the haptic have at least about 75% w/w of the same base polymer chain, and, when present, the same cross-linking agent.

15. An intraocular lens according to claim 1, wherein the interface portion of the optic and the interface portion of the haptic have at least about 90% w/w of the same base polymer chain, and, when present, the same cross-linking agent.

16. An intraocular lens according to claim 1, wherein a refractive index of the interface portion of the haptic is within 2% of the refractive index of the interface portion of the optic.

17. An intraocular lens comprising an optic having a clear aperture that comprises an inner portion and an outer portion disposed about said inner portion and an intermediate portion between the inner portion and the outer portion, the portions comprising a common polymeric material and have a common refractive index; wherein said inner portion and said outer portion each have a different modulus of elasticity, wherein the intermediate portion includes a modulus of elasticity gradient that varies along a radial direction extending from an inner region of the intermediate portion to an outer region of the intermediate portion, and wherein the entirety of said clear aperture is capable of contributing to a focused image when the intraocular lens is implanted in a capsular bag of an eye.

18. An intraocular lens according to claim 17, wherein the intraocular lens is movable under the normal muscle movement of the human eye.

19. An intraocular lens according to claim 17, wherein the intraocular lens is deformable under the normal muscle movement of the human eye.

20. An intraocular lens according to claim 17, wherein the portions of the clear aperture of the optic have at least about 75% w/w of the same base polymer chain, and, when present, the same cross-linking agent.

21. An intraocular lens according to claim 17, wherein the portions of the clear aperture of the optic have at least about 90% w/w of the same base polymer chain, and, when present, the same cross-linking agent.

22. An intraocular lens according to claim 17, wherein the refractive indices of the inner portion, outer portion, and intermediate portion of the clear aperture are within about 2% of each other.

23. An intraocular lens comprising an optic and a haptic,
wherein an interface portion of the haptic protrudes inside an interface portion of the optic,
wherein said interface portion of the optic has a lower modulus of elasticity than the interface portion of the haptic,
wherein at least the interface portion of the optic has a modulus of elasticity of less than about 100 kPa;
wherein said interface portion of said optic and said interface portion of said haptic comprise a common polymeric material and have a common refractive index, and wherein at least the interface portion of the optic that receives the haptic has an optical power for forming a focused image.

24. An intraocular lens according to claim 23, wherein the intraocular lens is movable under the normal muscle movement of the human eye.

25. An intraocular lens according to claim 23, wherein the intraocular lens is deformable under the normal muscle movement of the human eye.

26. An intraocular lens according to claim 23, wherein the interface portion of the optic and the interface portion of the haptic have at least about 75% w/w of the same base polymer chain, and, when present, the same cross-linking agent.

27. An intraocular lens according to claim 23, wherein the interface portion of the optic and the interface portion of the haptic have at least about 90% w/w of the same base polymer chain, and, when present, the same cross-linking agent.

28. An intraocular lens according to claim 23, wherein a refractive index of the interface portion of the haptic is within 2% of the refractive index of the interface portion of the optic.

* * * * *

UNITED STATES PATENT AND TRADEMARK OFFICE
CERTIFICATE OF CORRECTION

| | | |
|---|---|---|
| PATENT NO. | : 8,216,310 B2 | Page 1 of 1 |
| APPLICATION NO. | : 11/864450 | |
| DATED | : July 10, 2012 | |
| INVENTOR(S) | : Can B. Hu and Michael D. Lowery | |

It is certified that error appears in the above-identified patent and that said Letters Patent is hereby corrected as shown below:

In Column 19, line 50, the word "compex" should read -- complex --.

Signed and Sealed this
Fifth Day of February, 2013

Teresa Stanek Rea
*Acting Director of the United States Patent and Trademark Office*